US009624236B2

(12) United States Patent
Parthasaradhi Reddy et al.

(10) Patent No.: US 9,624,236 B2
(45) Date of Patent: Apr. 18, 2017

(54) AMORPHOUS DARUNAVIR (75) Inventors: Bandi Parthasaradhi Reddy, Andhra Pradesh (IN); Kura Rathnakar Reddy, Andhra Pradesh (IN); Dasari Muralidhara Reddy, Andhra Pradesh (IN); Rapolu Raji Reddy, Andhra Pradesh (IN); Kesireddy Subash Chander Reddy, Andhra Pradesh (IN); Bandi Vamsi Krishna, Andhra Pradesh (IN)

(73) Assignee: HETERO RESEARCH FOUNDATION, Balanagar, Hyderabad, Andhra Pradesh (IN)

( * ) Notice: Subject to any disclaimer, the term of this patent is extended or adjusted under 35 U.S.C. 154(b) by 664 days.

(21) Appl. No.: 13/530,844

(22) Filed: Jun. 22, 2012

(65) Prior Publication Data

US 2012/0288563 A1 Nov. 15, 2012

Related U.S. Application Data (63) Continuation-in-part of application No. 13/128,157, filed as application No. PCT/IN2009/000724 on Dec. 16, 2009, now abandoned, application No. 13/530,844, which is a continuation-in-part of application No. PCT/IN2009/000299, filed on May 10, 2010.

(51) Int. Cl.
*A01N 43/08* (2006.01)
*A61K 31/34* (2006.01)
*C07D 493/04* (2006.01)
*A61K 9/20* (2006.01)

(52) U.S. Cl.
CPC .......... *C07D 493/04* (2013.01); *A61K 9/2027* (2013.01); *A61K 9/2054* (2013.01); *A61K 31/34* (2013.01)

(58) Field of Classification Search
CPC ..... A61K 9/2054; A61K 31/34; A61K 9/2027
USPC ........................................................ 514/470
See application file for complete search history.

(56) References Cited

U.S. PATENT DOCUMENTS

| | | | |
|---|---|---|---|
| 3,876,632 A | 4/1975 | Sturm et al. | |
| 4,670,578 A | 6/1987 | Budavari et al. | |
| 4,692,438 A * | 9/1987 | Hassall et al. ................ | 514/183 |
| 5,315,016 A | 5/1994 | Hansen et al. | |
| 6,248,775 B1 | 6/2001 | Vazquez et al. | |
| 7,649,010 B2 | 1/2010 | Chen et al. | |
| 7,700,645 B2 | 4/2010 | Vermeersch et al. | |
| 2003/0125336 A1 | 7/2003 | Fleitz et al. | |
| 2005/0250845 A1* | 11/2005 | Vermeersch et al. ......... | 514/456 |
| 2008/0269322 A1 | 10/2008 | De Kock et al. | |
| 2009/0111796 A1 | 4/2009 | Muto et al. | |
| 2010/0094028 A1 | 4/2010 | Lemaire et al. | |
| 2011/0313035 A1 | 12/2011 | Reddy et al. | |
| 2012/0088808 A1 | 4/2012 | Pichler et al. | |
| 2012/0288563 A1 | 11/2012 | Reddy et al. | |
| 2013/0072552 A1 | 3/2013 | Parthasaradhi Reddy et al. | |

FOREIGN PATENT DOCUMENTS

| | | | |
|---|---|---|---|
| EP | 0715618 B1 | | 12/1998 |
| WO | 9967417 A2 | | 12/1999 |
| WO | 03106461 A2 | | 12/2003 |
| WO | WO 2006/067795 | * | 6/2006 |
| WO | WO 2007/054969 | * | 5/2007 |
| WO | WO 2010/086844 | * | 8/2010 |
| WO | 2011073993 A1 | | 6/2011 |

OTHER PUBLICATIONS

Yu (Advanced Drug Delivery Reviews (2001) 48:27-42).*
Ghosh et al.; "Potent HIV Protease Inhibitors Incorporating High-Affinity P2-ligands and (R)-(hydroxyethylamino) sulfonamide Isostere"; Bioorganic and Medicinal Chemistry Letters; 8(6); pp. 687-690; (1998).
U.S. Appl. No. 13/128,157, filed Jul. 6, 2011; NonFinal Office Action of Jun. 10, 2013; 40 pages.
Vippagunta et al.; "Crystalline Solids"; Advanced Drug Delivery Reviews; 48; pp. 3-26; (2001).
U.S. Appl. No. 14/047,243, filed Oct. 7, 2013.
U.S. Appl. No. 13/128,157, filed Jul. 6, 2011; Final Office Action of Oct. 22, 2013.

* cited by examiner

*Primary Examiner* — Marcos Sznaidman
(74) *Attorney, Agent, or Firm* — Cantor Colburn LLP (57) ABSTRACT

Described herein is pure amorphous darunavir, methods of making pure amorphous darunavir and pharmaceutical compositions containing amorphous darunavir and a pharmaceutically acceptable excipient.

3 Claims, 3 Drawing Sheets

AMORPHOUS DARUNAVIR

CROSS-REFERENCE TO RELATED APPLICATIONS

The present application is a continuation in part of U.S. application Ser. No. 13/128,157, filed on Jul. 6, 2011, which is a 371 of PCT/IN2009/000724, filed on Dec. 16, 2009 under the provisions of 35 U.S.C. §119 and the International Convention for the protection of Industrial Property, and is also a continuation in part of PCT/IN2009/000299, filed on May 10, 2010, which are incorporated herein by reference in their entirety.

FIELD OF THE DISCLOSURE

The present disclosure provides novel solvated and amorphous forms of darunavir and processes for their preparation.

BACKGROUND

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections. Darunavir has HIV protease inhibitory activity and is particularly well suited for inhibiting the HIV-1 and HTV-2 viruses. Chemically darunavir is (1S,2R,3'R,3'aS,6'aR)-[3'-hexahydrofuro[2,3-b]furanyl-[3-(4-aminobenzenesulfonyl)isobutylamino]-1-benzyl-2-hydroxypropyl]carbamate. Darunavir is represented by the following structure:

Processes for the preparation of darunavir were disclosed in EP 715618, WO 99/67417, U.S. Pat. No. 6,248,775, and in Bioorganic and Chemistry Letters, Vol. 8, pp. 687-690, 1998, "Potent HIV protease inhibitors incorporating high-affinity P2-ligands and (R)-(hydroxyethylamino)sulfonamide isostere", all of which are incorporated herein by reference.

Darunavir can exist in different polymorphic forms, which differ from each other in terms of stability, physical properties, spectral data and methods of preparation.

U.S. Patent Publication No. 2005/0250845 described pseudopolymorphs of darunavir including Form A (ethanolate), Form B (hydrate), Form C (methanolate), Form D (acetonate), Form E (dichloromethanate), Form F (ethylacetate solvate), Form G (1-ethoxy-2-propanolate), Form H (anisolate), Form I (tetrahydrofuranate), Form J (isopropanolate) and Form K (mesylate) of darunavir. Pseudopolymorphs are distinguished from polymorphs and defined as crystalline forms having solvent molecules incorporated into the crystalline lattice.

One object of the present disclosure is to provide novel solvated forms of darunavir and processes for their preparation.

Another object of the present disclosure is to provide a novel composition and process for pure amorphous darunavir pharmaceutical compositions comprising them.

SUMMARY

In one aspect, provided herein is a darunavir $C_5$-$C_8$ alcohol solvate.

In another aspect, provided herein is a process for preparing a darunavir $C_5$-$C_8$ alcohol solvate, which comprises crystallizing the darunavir $C_5$-$C_8$ alcohol solvate from a solution of darunavir in a $C_5$-$C_8$ alcohol solvent.

In a further aspect, provided herein is a pure amorphous darunavir.

In another aspect, provided herein is a process for preparing a pure darunavir amorphous form, which comprises:
 a) dissolving darunavir in a first solvent to provide a solution;
 b) distilling the first solvent from the solution obtained in step (a) to obtain a residue;
 c) slurrying the residue obtained in step (b) with second solvent selected from an aliphatic solvent or aromatic solvent, wherein the second solvent does not form a solvate with darunavir; and
 d) isolating pure amorphous darunavir from the slurry in step (c).

In yet another aspect, provided herein is a pharmaceutical composition comprising a pure darunavir amorphous form and a pharmaceutically acceptable excipient.

BRIEF DESCRIPTION OF THE DRAWINGS

The above-described and other features will be appreciated and understood by those skilled in the art from the following detailed description, drawings, and appended claims.

DETAILED DESCRIPTION

According to one aspect, there is provided a darunavir $C_5$-$C_8$ alcohol solvate.

According to another aspect, there is provided a process for preparing a darunavir $C_5$-$C_8$ alcohol solvate, which comprises crystallizing the darunavir $C_5$-$C_8$ alcohol solvate from a solution of darunavir in a $C_5$-$C_8$ alcohol solvent.

Solvates can occur in different ratios of solvation. The ratio of darunavir to the $C_5$-$C_8$ alcohol solvent may range between 1:0.3 and 1:1.3. In particular, the ratio may range from about 0.5 to about 1 molecules of $C_5$-$C_8$ alcohol solvent per 1 molecule of darunavir, preferably the ratio is 1 molecule of $C_5$-$C_8$ alcohol solvent per 1 molecule of darunavir.

The $C_5$-$C_8$ alcohol solvent is selected from 2-methyl-2-butanol or n-pentanol.

Figure 1:
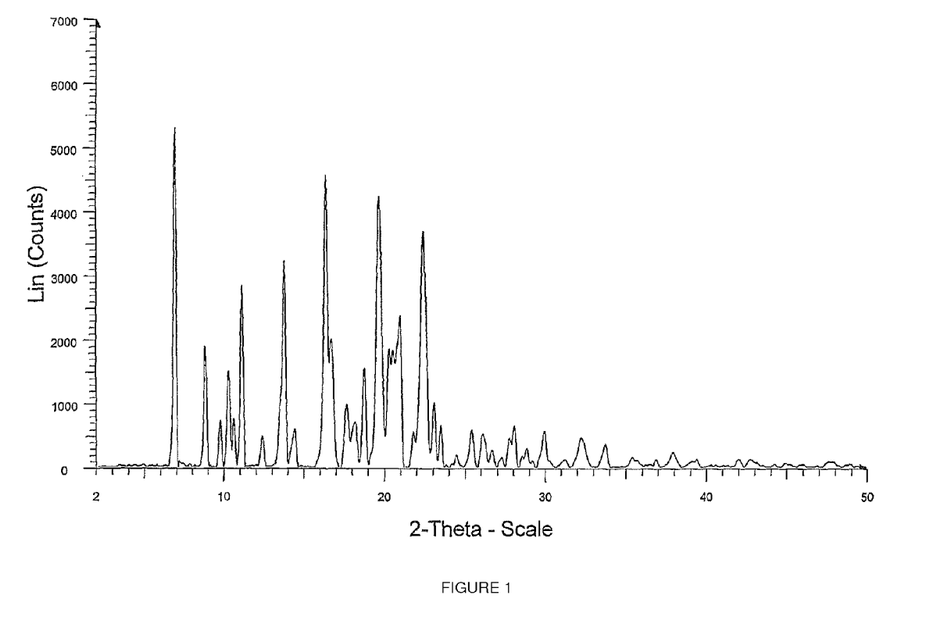
FIG. 1 is X-ray powder diffraction spectrum of darunavir 2-methyl-2-butanol solvate.

Darunavir 2-methyl-2-butanol solvate is characterized by peaks in the powder x-ray diffraction spectrum having 2Θ angle positions at about 6.8, 8.8, 11.1, 13.7, 16.3, 16.7, 19.6, 20.9 and 22.3±0.2 degrees. The powder x-ray diffractogram (PXRD) of darunavir 2-methyl-2-butanol solvate is shown in FIG. 1.

Figure 2:
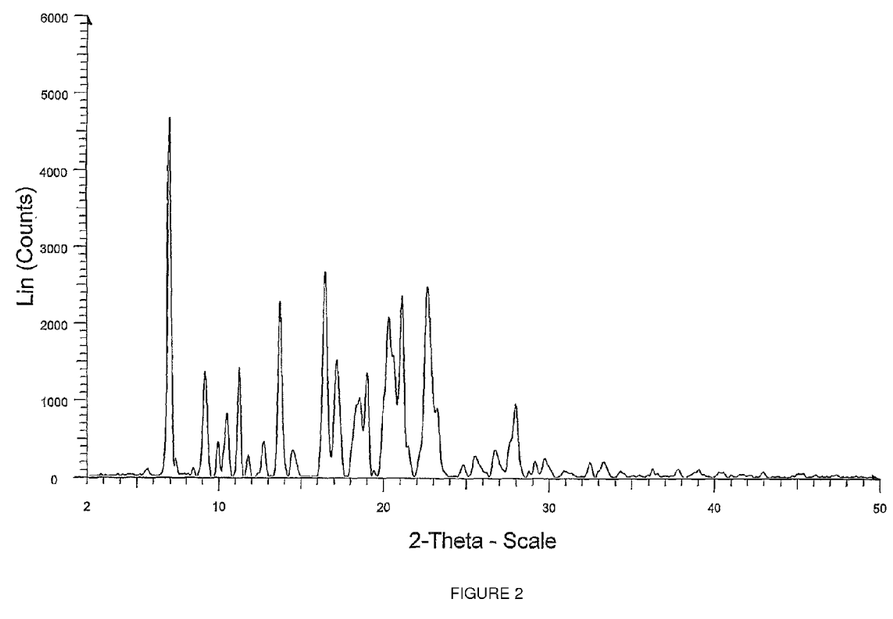
FIG. 2 is X-ray powder diffraction spectrum of darunavir n-pentanol solvate.
Figure 3:
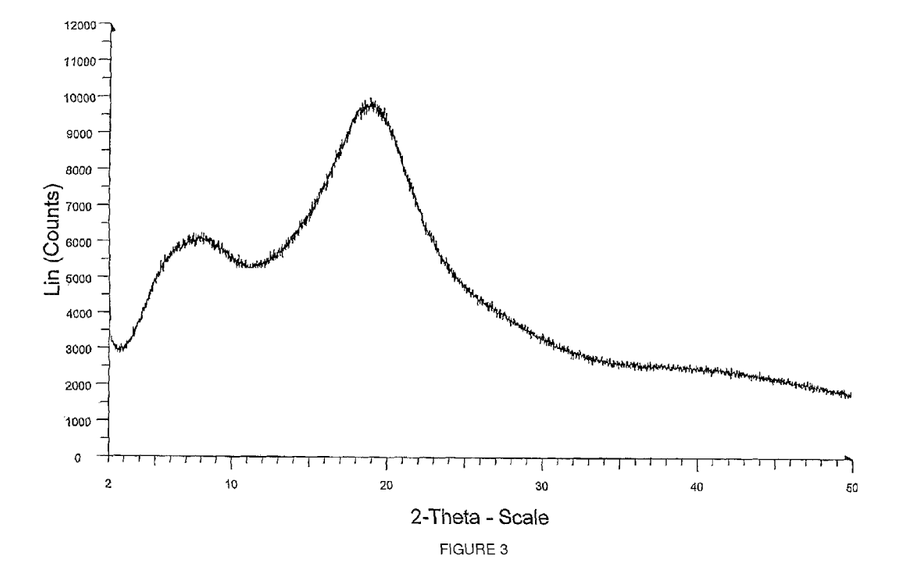
FIG. 3 is X-ray powder diffraction spectrum of pure darunavir amorphous form.

Darunavir n-pentanol solvate is characterized by peaks in the powder x-ray diffraction spectrum having 2Θ angle positions at about 6.9, 9.1, 11.2, 13.7, 16.4, 17.1, 20.3, 20.6, 21.1 and 22.6±0.2 degrees. The powder x-ray diffractogram (PXRD) of darunavir n-pentanol solvate is shown in FIG. 2.

The solvates described herein are useful intermediates for obtaining pure darunavir. The solvates of darunavir described herein can be used to obtain known polymorphs of darunavir.

Also included herein is pure amorphous darunavir. By pure, it is meant polymorphically pure and/or free from impurities. By polymorphically pure, it is meant that the pure amorphous darunavir is substantially free from crystalline darunavir polymorphs, including solvates, wherein the pure amorphous darunavir contains less than 10%, less than 5%, or less than 2% crystalline polymorphs of darunavir as measured by powder x-ray diffraction. Free from impurities means that the pure amorphous darunavir is free from solvents, including water, that is, the pure amorphous darunavir is solvent-free and anhydrous. The pure amorphous darunavir free from impurities contains greater than 98%, specifically greater than 99% and more specifically greater than 99.8% darunavir.

As described in U.S. Patent Publication No. 2005/0250845, darunavir readily forms solvates with solvents such as ethanol, water, methanol, acetone, dichloromethane, ethyl acetate, and the like. These previously characterized crystalline forms of darunavir contain a percentage of solvent in the crystalline lattice which may be undesirable in the production of pharmaceutical dosage forms. It has been unexpectedly discovered herein that the use of solvents that do not form solvates with darunavir allow the production of pure amorphous darunavir, that is, darunavir that is polymorphically pure and also free from impurities including solvent. Thus, pharmaceutical compositions containing pure darunavir as described herein do not suffer from the disadvantages of solvent carry-over from solvated forms.

According to another aspect, there is provided a process for the preparation of pure amorphous darunavir, which comprises:
a) dissolving darunavir in a first solvent to produce a solution;
b) distilling the first solvent from the solution obtained in step (a) to obtain a residue;
c) slurrying the residue obtained in step (b) with second solvent selected from an aliphatic solvent or aromatic solvent, wherein the second solvent does not form a solvate with darunavir; and
d) isolating pure amorphous darunavir from the slurry in step (c).

The darunavir used in step (a) is darunavir in any solvated or hydrated- or anhydrous form.

In one embodiment the, the darunavir used in step (a) is a darunavir $C_5$-$C_8$ alcohol solvate such as the 2-methyl-2-butanol solvate or n-pentanol solvate.

The solvent used in step (a) may be a solvent or mixture of solvents selected from the group consisting of dichloromethane, ethylene dichloride, chloroform and ethyl acetate. A specific solvent is dichloromethane.

Removing the solvent in step (b) may be distillation at atmospheric pressure or at reduced pressure. The distillation may be carried out until the solvent is almost completely distilled off, specifically completely distilled off.

The aliphatic solvent or aromatic solvent used in step (c) may be a solvent or a mixture of solvents selected from the group consisting of cyclohexane, hexane, n-heptane, toluene and xylene. A specific aliphatic solvent is cyclohexane.

The isolation of darunavir amorphous form may be performed by conventional techniques such as centrifugation and filtration.

According to another aspect, there is provided a pharmaceutical composition comprising pure amorphous darunavir and a pharmaceutically acceptable excipient.

In one embodiment, a stable pharmaceutical composition comprises pure amorphous darunavir and a pharmaceutically acceptable excipient, wherein the pure amorphous darunavir contains less than 10%, less than 5% or less than 2% crystallinity after storage for 1 month, 2 months, 6 months, 9 months or even one year. The amount of crystallinity can be measured, for example, by x-ray powder diffraction.

In one embodiment, also provided is an oral pharmaceutical composition comprising amorphous darunavir, specifically polymorphically pure darunavir, having a $d_{90}$ particle size of about 150 μm to 250 μm. In one aspect, the amorphous has a particle size of 175 to 225 μm, specifically 190 to 200 μm.

In one aspect, the oral pharmaceutical composition is a solid oral dosage form, such as a tablet which is optionally film coated.

The oral pharmaceutical composition of amorphous darunavir may be prepared by direct compression, wet granulation or roll compaction. Specifically, the oral pharmaceutical composition of amorphous darunavir is prepared by direct compression.

The oral pharmaceutical composition may contain one or more additional excipients such as diluents, binders, disintegrants and lubricants. Exemplary diluents include lactose, sucrose, glucose, mannitol, sorbitol, calcium carbonate, microcrystalline cellulose such as Prosolv®, magnesium stearate and mixtures thereof. Specifically, the diluent is Prosolv®. Exemplary binders are selected from L-hydroxy propyl cellulose, polyvinyl pyrrolidine, hydroxylpropyl methyl cellulose, hydroxylethyl cellulose and pre-gelatinized starch. Exemplary disintegrants are selected from croscarmellose sodium, crospovidone, sodium starch glycolate and low substituted hydroxylpropyl cellulose. In a specific embodiment, the disintegrant is low substituted hydroxylpropyl cellulose and crospovidone. Exemplary lubricants are selected from sodium stearyl fumarate, magnesium stearate, zinc stearate, calcium stearate, stearic acid, talc, glyceryl behenate and colloidal silicon dioxide. A specific lubricant is selected from magnesium stearate, zinc stearate, calcium stearate and colloidal silicon dioxide.

In a specific embodiment, the oral pharmaceutical composition comprises amorphous darunavir, specifically pure amorphous darunavir, Prosolv®, crospovidone, colloidal silicon dioxide and magnesium stearate.

In one embodiment, the pharmaceutical composition is made by wet granulation. In a specific embodiment, the wet granulation process includes wet granulation of amorphous darunavir with the excipient(s), lubrication and followed by compression.

In another embodiment, the pharmaceutical composition is made by compaction. In a specific embodiment, the compaction process includes compaction of amorphous darunavir with the excipient(s), lubrication and followed by compression.

In yet another embodiment, the pharmaceutical composition is made by direct compression. In a specific embodiment, the direct compression process includes blending amorphous darunavir with the excipient(s), lubrication and followed by compression.

The tablet composition is optionally film coated such as with Opadry II orange.

The invention will now be further described by the following examples, which are illustrative rather than limiting.

XRPD:

X-ray powder diffraction spectra were measured on a Bruker axs D8 advance X-ray powder diffractometer having a copper-Kα radiation. Approximately 1 g of sample was gently flattered on a sample holder and scanned from 2 to 50 degrees two-theta, at 0.02 degrees to theta per step and a step of 10.4 seconds. The sample was simply placed on the sample holder. The sample was rotated at 30 rpm at a voltage 40 KV and current 35 mA.

Preparative Example: Preparation of Darunavir

To a mixture of (3R,3aS,6aR)-hexandrofuro[2,3-b]furan-3-ol (25 gm) and acetonitrile (180 ml) was added disuccinimidyl carbonate (56 gm) and pyridine (46 gm) at 25 to 30° C. The mixture was stirred for 1 hour at 25 to 30° C. and cooled to 0° C. A solution of 4-amino-N-((2R,3S)-3-amino-2-hydroxy-4-phenylbutyl)-N-(isobutyl)benzene sulfonamide (70 gm) in acetonitrile (300 ml) was added to the reaction mass at 0 to 5° C. for 30 minutes. To the reaction mass was added triethylamine (19 gm) and monomethylamine (3 gm) at 0 to 5° C., and the temperature was slowly raised to 25 to 30° C. and stirred for 22 hours. The solvent was distilled off completely under vacuum at 45° C. to provide a residue and to the residue was added ethyl acetate (250 ml). The ethyl acetate layer was washed with 10% sodium bicarbonate (100 ml), 2% sulfuric acid (100 ml), 10% sodium sulfate (100 ml) and 10% sodium chloride solution (100 ml). The layer was dried over sodium sulfate. The layer was treated with carbon and the solvent was distilled off under vacuum at below 45° C. to provide 85 g of darunavir.

EXAMPLES

Example 1

Preparation of Darunavir 2-Methyl-2-Butanol Solvate

Darunavir (85 g) as obtained in the preparative example was added to 2-methyl-2-butanol (50 ml) and the solvent was distilled off under vacuum at below 45° C. to provide a residue. To the residue was added 2-methyl-2-butanol (150 ml) and the slurry was heated to 50° C. The reaction mass was slowly cooled to room temperature and stirred for 24 hours. The reaction mass was further cooled to 0° C. and stirred for 1 hour at 0 to 5° C. The separated solid was filtered, washed with 2-methyl-2-butanol, and the solid was dried under vacuum at 50° C. to provide 60 g of darunavir 2-methyl-2-butanol solvate.

Example 2

Preparation of Darunavir N-Pentanol Solvate

Darunavir (85 g) as obtained in the preparative example was added to n-pentanol (50 ml) and the solvent was distilled off under vacuum at below 45° C. to provide a residue. To the residue was added n-pentanol (150 ml) and the slurry was heated to 50° C. The reaction mass was slowly cooled to room temperature and stirred for 24 hours. The reaction mass was further cooled to 0° C. and stirred for 1 hour at 0 to 5° C., and filtered. The solid obtained was washed with n-pentanol and dried under vacuum at 50° C. to provide 61 g of darunavir n-pentanol solvate.

Example 3

Preparation of Darunavir Amorphous Form

Darunavir 2-methyl-2-butanol solvate (5 g) as obtained in example 1 was dissolved in methylene dichloride (50 ml), and the methylene dichloride layer was dried over sodium sulfate. The layer was treated with carbon and the solvent was distilled off under vacuum at 45° C. to provide a foam-like residue. Cyclohexane (2×25 ml) was added to the residue, the solvent was distilled off, and the residue was collected. To the residue obtained was added cyclohexane (50 ml), with stirring for 30 hours at 20 to 25° C. The separated solid was filtered, washed with cyclohexane, and then dried under vacuum at 50° C. for 12 hours to provide 4.2 g of darunavir amorphous form.

Example 4

Preparation of Darunavir Amorphous Form

Darunavir n-pentanol solvate (5 g) as obtained in example 2 was dissolved in methylene dichloride (50 ml), and the methylene dichloride layer was dried over sodium sulfate. The layer was treated with carbon and distilled solvent was distilled off under vacuum at 45° C. to provide a foam like residue. Cyclohexane (2×25 ml) was added to the residue, distilled off the solvent and the residue was collected. To the residue obtained was added cyclohexane (50 ml), stirred for 30 hours at 20 to 25 C, filtered, washed with cyclohexane and dried under vacuum at 50° C. for 12 hours to provide 4.2 g of darunavir amorphous form.

Example 5

Preparation of Darunavir Amorphous Form

Example 3 was repeated using darunavir ethanolate form A instead of darunavir 2-methyl-2-butanol solvate to provide darunavir amorphous form.

Example 6

Preparation of Darunavir Amorphous Form

Example 3 was repeated using darunavir hydrated form B instead of darunavir 2-methyl-2-butanol solvate to provide darunavir amorphous form.

Example 7

Darunavir Composition

| Ingredients | Quantity/Unit (mg) |
|---|---|
| Amorphous darunavir* | 600.00 |
| Prosolv ® | 583.75 |

-continued

| | Quantity/Unit (mg) |
|---|---|
| Crospovidone | 37.50 |
| Purified water | q.s |
| Colloidal silicon dioxide | 25.00 |
| Magnesium stearate | 3.75 |
| Film coating | |
| Opadry ® II orange | 25.00 |
| Total Tablet weight | 1275.00 |

*Particle size distribution of amorphous darunavir: $d_{10}$-11 µm; $d_{50}$-50 µm $d_{90}$-195 µm The process of the preparation involve following steps:
i). Blending of amorphous darunavir, Prosolv®, crospovidone dried if necessary
ii). Lubricating with colloidal silicon dioxide and magnesium stearate
iii). Compressing the lubricated blend of step (ii) into tablets.
iv). Coating the compressed tablets with Opadry®.

Example 8

Alternative Darunavir Composition

| | Quantity/Unit (mg) |
|---|---|
| Ingredients | |
| Amorphous darunavir* | 600.00 |
| Prosolv ® | 596.25 |
| Crospovidone | 25.00 |
| Purified water | q.s |
| Colloidal silicon dioxide | 25.00 |
| Magnesium stearate | 3.75 |
| Film coating | |
| Opadry ® II orange | 25.00 |
| Total Tablet weight | 1275.00 |

*Particle size distribution of amorphous darunavir: $d_{10}$-15 µm; $d_{50}$-60 µm $d_{90}$-210 µm The process of the preparation involve following steps:
i). Granulation of amorphous darunavir, Prosolv®, crospovidone with a suitable solvent.
ii). Lubricating with colloidal silicon dioxide and magnesium stearate
iii). Compressing the lubricated blend of step (ii) into tablets.
iv). Coating the compressed tablets with Opadry®.

Example 9

Second Alternative Darunavir Composition

| | Quantity/Unit (mg) |
|---|---|
| Ingredients | |
| Amorphous darunavir* | 600.00 |
| Prosolv ® | 608.75 |
| Crospovidone | 25.00 |
| Purified water | q.s |
| Colloidal silicon dioxide | 12.50 |
| Magnesium stearate | 3.75 |

-continued

| | Quantity/Unit (mg) |
|---|---|
| Film coating | |
| Opadry ® II orange | 25.00 |
| Total Tablet weight | 1275.00 |

*Particle size distribution of amorphous darunavir: $d_{10}$-17 µm; $d_{50}$-65 µm $d_{90}$-213 µm The process of the preparation involve following steps:
i). Compaction of Darunavir, Prosolv®, crospovidone with a suitable solvent.
ii). Lubricating with colloidal silicon dioxide and magnesium stearate
iii). Compressing the lubricated blend of step (ii) into tablets.
iv). Coating the compressed tablets with Opadry.

Example 10

Third Alternative Darunavir Composition

| | Quantity/Unit (mg) |
|---|---|
| Ingredients | |
| Amorphous darunavir* | 600.00 |
| Microcrystalline cellulose | 571.75 |
| Crospovidone | 37.50 |
| Purified water | q.s |
| Colloidal silicon dioxide | 37.00 |
| Magnesium stearate | 3.75 |
| Film coating | |
| Opadry ® II orange | 25.00 |
| Total Tablet weight | 1275.00 |

*Particle size distribution of amorphous darunavir: $d_{10}$-8 µm; $d_{50}$-45 µm $d_{90}$-182 µm The process of the preparation involve following steps:
i). Blending of amorphous darunavir, microcrystalline cellulose, crospovidone and dried if necessary
ii). Lubricating with colloidal silicon dioxide and magnesium stearate
iii). Compressing the lubricated blend of step (ii) into tablets.
iv). Coating the compressed tablets with Opadry®.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

As used herein, a polymorph is a crystalline form of an active pharmaceutical ingredient having a distinguishable crystalline form, and includes crystalline polymorphs, amorphous forms, as well as solvate and hydrate forms, which are often referred to as pseudopolymorphs. Solvates are crystalline forms containing a stoichiometric or nonstoichiometric amount of solvent. A hydrate is a solvate wherein the solvent is water.

Amorphous forms are disordered forms that do not have a distinguishable crystalline lattice. Amorphous materials typically do not have sharp, well-defined reflections in their x-ray diffraction patterns, but rather a broad peak spanning a range of two-theta angles.

In general, each polymorphic form, including solvates, has its own characteristic x-ray diffraction pattern. For active pharmaceutical ingredients, powder x-ray diffraction is the most commonly used tool for the identification and determination of the purity of crystalline materials. The intensity ratio and the d-spacings (Interplanar spacings) and/or 2-theta angles of the reflections in the x-ray powder diffraction pattern are used to compare a reference pattern to a sample. In general, two-theta values are reproducible to ±010 or 0.20 degrees. For a given active pharmaceutical ingredient, 10, 9, 8, 7, 6, 5, 4, 3, 2 or even 1 reflection may be sufficient to identify a particular polymorph compared to other polymorphs of the same active pharmaceutical ingredient.

Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

A "pharmaceutical composition" comprises an active pharmaceutical ingredient and a pharmaceutically acceptable excipient. The term "pharmaceutically acceptable excipient" includes a pharmaceutically acceptable material, composition or vehicle, suitable for administering an active pharmaceutical ingredient. Each excipient should be "acceptable" in the sense of being compatible with the other ingredients of the formulation and not injurious to the patient. Excipients include diluents, binders, disintegrants, glidants, lubricants, flavoring, and others.

Diluents increase the bulk of a solid pharmaceutical composition. Exemplary diluents for solid compositions include, but are not limited to, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Exemplary binders for solid pharmaceutical compositions include, but are not limited to, acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

Disintegrants increase the dissolution rate of a compacted solid pharmaceutical composition in the patient's stomach, for example. Exemplary disintegrants include, but are not limited to, alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®) and starch.

Glidants can be added to improve the flowability of a non-compacted solid composition and to improve the accuracy of dosing. Exemplary excipients that may function as glidants include colloidal silicon dioxide, magnesium trisilicate, powdered cellulose, starch, talc and tribasic calcium phosphate.

Compaction of a powdered composition into a tablet, for example, subjects the composition to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Exemplary lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the pharmaceutical compositions include maltol, vanillin, ethyl vanillin, menthol, citric acid, fumaric acid, ethyl maltol and tartaric acid.

Solid and liquid compositions may also be dyed using a pharmaceutically acceptable colorant to improve their appearance and/or facilitate patient identification of the product and unit dosage level.

In liquid pharmaceutical compositions, the active pharmaceutical ingredient and any other solid excipients are dissolved or suspended in a liquid carrier such as water, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel of the product and/or coat the lining of the gastrointestinal tract. Such agents include, but are not limited to, acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

A liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid compositions include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route is oral. The dosages may be conveniently presented in unit dosage form and prepared by methods well-known in the pharmaceutical arts.

Dosage forms include solid dosage forms like tablets, powders, capsules, suppositories, sachets, troches and lozenges, as well as liquid syrups, suspensions and elixirs. The dosage form may be a capsule containing the composition, such as a powdered or granulated solid composition, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

Compositions for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica.

Pharmaceutical dosage forms can vary in their release properties. By "immediate release composition" is meant a dosage form that is formulated to release substantially all the active pharmaceutical ingredient on administration with no enhanced, delayed or extended release effect.

Both "extended-release" and "delayed release" are modified or controlled forms of release. In extended-release, the drug is released over a period of time, such as, for example 4, 6, 10, 12, 15, 18, 21, or 24 hours, or more. Suitable materials for a release controlling layer include EUDRAGIT® RL (copolymers of acrylic and methacrylic acid esters), EUDRAGIT® RS (copolymers of acrylic and methacrylic acid esters), cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®, and the like.

"Delayed release" is release delayed for a period of time after administration and can be accomplished, for example, by applying a coating of enteric materials. "Enteric materials" are polymers that are substantially insoluble in the acidic environment of the stomach, but are predominantly soluble in intestinal fluids at various specific pHs. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, co-polymerized methacrylic acid/methacrylic acid methyl esters such as, for instance, materials known under the trade name EUDRAGIT®L12.5, L100, or EUDRAGIT®S12.5, S100, and several commercially available enteric dispersion systems (e.g., EUDRAGIT® L30D55, EUDRAGIT® FS30D, EUDRAGIT® L100-55, EUDRAGIT® S100 (Rohm Pharma), KOLLICOAT® MAE30D and 30DP (BASF), ESTACRYL® 30D (Eastman Chemical), AQUATERIC® and AQUACOAT® CPD30 (FMC)).

In certain cases, dosage forms can have both immediate-release and controlled-release properties, such as a combination of immediate-release and controlled-release pellets.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A process for preparing a pure darunavir amorphous form, comprising
   a) dissolving darunavir in a first solvent to provide a solution, wherein the first solvent is dichloromethane, ethylene dichloride, chloroform, ethyl acetate, or a mixture thereof;
   b) distilling the first solvent from the solution obtained in step (a) to provide a residue;
   c) slurrying the residue obtained in step (b) with second solvent selected from an aliphatic solvent or aromatic solvent, wherein the second solvent does not form a solvate with darunavir, and wherein the second solvent is cyclohexane, hexane, n-heptane, toluene, xylene, or a mixture thereof; and
   d) isolating pure amorphous darunavir from the slurry in step (c), wherein the pure amorphous darunavir contains less than 5% crystalline polymorphs of darunavir as measured by powder x-ray diffraction.

2. The process of claim 1, wherein the solvent used in step (a) is dichloromethane.

3. The process of claim 1, wherein the second solvent is cyclohexane.

* * * * *